United States Patent [19]

Sikes

[11] Patent Number: 5,648,082

[45] Date of Patent: Jul. 15, 1997

[54] POLYAMINO ACID DISPERSANTS

[75] Inventor: C. Steven Sikes, Mobile, Ala.

[73] Assignee: University of South Alabama, Mobile, Ala.

[21] Appl. No.: 573,120

[22] Filed: Dec. 15, 1995

Related U.S. Application Data

[63] Continuation of Ser. No. 114,359, Sep. 1, 1993, abandoned, which is a continuation of Ser. No. 658,659, Feb. 19, 1991, Pat. No. 5,328,690.

[51] Int. Cl.$^6$ ............................................. A61K 7/06
[52] U.S. Cl. ........................... 424/401; 424/405; 424/421; 424/70.14
[58] Field of Search ....................... 424/70, 71, 401, 424/687, 689, 647, 648; 528/328, 340; 252/47, 302–304; 524/606; 514/7; 530/324

[56] References Cited

U.S. PATENT DOCUMENTS

| | | | |
|---|---|---|---|
| 4,678,840 | 7/1987 | Fong et al. | 525/340 |
| 4,735,797 | 4/1988 | Grollier et al. | 424/47 |
| 4,868,287 | 9/1989 | Sikes et al. | 530/324 |
| 5,051,401 | 9/1991 | Sikes | 514/7 |
| 5,328,690 | 7/1994 | Sikes | 424/401 |

*Primary Examiner*—Neil S. Levy
*Attorney, Agent, or Firm*—Oblon, Spivak, McClelland, Maier & Neustadt, P.C.

[57] ABSTRACT

Polyamino acids of the formulae (I) and (II):

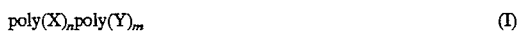

$$\text{poly}(X)_n\text{poly}(Y)_m \qquad (I)$$

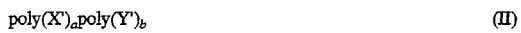

$$\text{poly}(X')_a\text{poly}(Y')_b \qquad (II)$$

wherein each X independently is a polar amino acid, each Y independently is a non-polar amino acid, each X' independently is a polar amino acid, and each Y' independently is a phosphorylated amino acid, and salts of these polyamino acids, are effective as dispersing agents for minerals in aqueous media and for stabilizing aqueous suspensions of minerals.

6 Claims, 5 Drawing Sheets

POLYAMINO ACID DISPERSANTS

This is a continuation of application Ser. No. 08/114,359 filed on Sep. 1, 1993, abandoned, which is a continuation of application Ser. No. 07/658,659 filed on Feb. 21, 1991, now U.S. Pat. No. 5,328,690.

BACKGROUND OF THE INVENTION

1. Field of the Invention

The present invention relates to a method for dispersing mineral particles by using polyamino acids as dispersing agents. This includes mineral dispersions in aqueous media, detergent compositions for dispersion of soil particles, dispersion of pigments in cosmetics and paints, and dispersion of minerals in making paper.

2. Discussion of the Background

Dispersions of particles in aqueous and other media are important in many applications; e.g., paints, detergents, cosmetics, and paper. In addition, methods for dispersing mineral particles in aqueous media are important for the prevention of corrosion and scaling of cooling and boiler equipment. Particular problems may arise when the aqueous sample contains more than one kind of mineral particle.

The importance of keeping minerals dispersed in aqueous media has led to much work in this area, and the use of polymers as dispersing agents has been explored. Thus, Bendiksen and Parsons, *Proceedings of ACS Division of Polymeric Materials*, Vol. 57, pp. 719–725, (1987) disclose the use of sulfonic acid/acrylic acid copolymers and poly (acrylic acid) as dispersing agents for clay and iron oxide. Masler et al., *Corrosion* 88, paper no. 11, NACE (1988) disclose the use of various acrylic acid copolymers and sulfonated styrene copolymers as dispersing agents for calcium phosphonate. Smyk et al., *Corrosion* 88, paper no. 14, NACE (1988) disclose the use of various terpolymers which contain monomers derived from acrylic acid as dispersing agents for a variety of minerals. Hoots et al., *Corrosion* 89, paper no. 175, NACE (1989) discuss the mechanisms by which conventional dispersing agents disperse minerals in aqueous media. U.S. Pat. No. 3,839,215 discloses the use of poly-α-hydroxyacrylic acid in detergents to sequester metal ions.

The use of polymers based on amino acids as dispersing agents has also been studied. U.S. Pat. No. 4,640,943 discloses the use of polyaspartic acid and polyglutamic acid as surface modifiers for improving the wettability and enhancing the dispersibility of inorganic fillers. German Patent Application DE 37 24 460 discloses the use of polyglutamic acid and polyaspartic acid and their salts as components in wetting compositions which are useful in cleansing and detergent compositions.

U.S. Pat. Nos. 4,428,749 and 4,732,693 disclose the use of polyaspartic acid as an antiredeposition agent in detergent compositions.

Japanese Patent Application Kokai 59-209635 discloses the use of wetting agents which contain polyglutamic acid in shampoos and rinses in hair or skin lotions and in solid or liquid detergents.

U.S. Pat. No. 3,846,380 discloses the use of terminal group derivatized polyaspartic acid and derivatives of polyaspartic acid which may be enriched in polyaspartic acid for use as foaming agents, solubilizing agents, dispersing agents, emulsifying agents, rust-proofing agents, fiber-treating agents, level dying agents, and retarding agents.

*Chemical Abstract* Vol. 79, 55246 broadly discloses the use of poly(amino acids) as surfactants in detergents in cosmetics. In particular, the use of polyaspartic acid and polyaspartic acid derivatives as surfactants is disclosed.

German Patent Application DE 36 26 672 discloses the use of polyaspartic acid amide and its salt derivatives as a scale remover.

U.S. Pat. No. 4,363,797 discloses the use of polyaspartic acid derivatives which may contain free polyaspartic acid units as a component in shampoos and rinsing lotions.

Japanese Patent Application Kokai 50-38520 discloses photographic compositions which contain polyglutamic acid derivatives and pigment powders.

Japanese Patent Application Kokai 63-28890 discloses the use of polyamino carboxylic acids for the removal of carbonate scale from a geothermal power generation plant.

SUMMARY OF THE INVENTION

Accordingly, one object of the present invention is to provide dispersing agents for stabilizing aqueous dispersions of minerals.

It is another object of the present invention to provide a method for stabilizing aqueous mineral dispersions.

It is another object of the present invention to provide stabilized aqueous mineral dispersions.

It is another object of the present invention to provide stable dispersions of minerals in aqueous media which contain a dispersing agent based on polyamino acids.

It is another object of the present invention to provide detersive systems which contain such dispersing agents.

It is another object of the present invention to provide cosmetics which contain such dispersing agents.

These and other objects, which will become apparent during the course of the following detailed description, have been achieved by the Inventor's discovery that polyamino acids of the formulae (I) and (II):

$$\text{poly}(X)_n\text{poly}(Y)_m \qquad (I)$$

where each X independently is aspartic acid, glutamic acid, phosphoserine, phosphohomoserine, phosphotyrosine, or phosphothreonine, each Y independently is alanine, leucine, isoleucine, valine, glycine or other nonpolar, amino acid residues, n is 2 to 60, m is 2 to 60, and n+m is ≧5, and wherein poly $(X)_n$ may contain up to 10% of the Y residues and poly $(Y)_m$ may contain up to 10% of the X residues, and salts thereof; and $$\text{poly}(X')_a\text{poly}(Y')_b \qquad (II)$$

where each X' independently is aspartate, glutamate, glutamine, asparagine, or anionic derivatives of these amino acids, or phosphoserine, each Y' independently is a phosphorylated amino acid such as phosphoserine, phosphohomoserine, phosphotyrosine, phosphothreonine, phosphoglutamine, phosphoasparagine or mixtures of these residues, a is 2 to 150, b is 1 to 3, and a+b is ≧5, and salts of these peptides; are effective as dispersing agents for minerals in aqueous media and for stabilizing aqueous suspensions of minerals.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein:

FIGS. 2 and 3 illustrate the efficacy of various dispersing agents for stabilizing an aqueous dispersion of iron oxide which also contains calcium. FIG. 2: $HO\text{-}Asp_{20}\text{-}Ala_8\text{-}NH_2$, 1 μg/ml, ●; $HO\text{-}Asp_{30}\text{-}Ala_8\text{-}NH_2$, 1 μg/ml, ▲; $HO\text{-}Asp_{20}\text{-}Ala_{20}\text{-}NH_2$, 1 μg/ml, △; and thermal polyasp, 1 μg/ml, ○. FIG. 3: $Asp_{20}\text{-}Ala_8$, ▲; industrial terpolymer, +; polyaspartate, △; and polyacrylate, +.

DETAILED DESCRIPTION OF THE PREFERRED EMBODIMENTS

Thus, the general structure of the polypeptides of the present invention may be represented by formulae (I) and (II):

$$\text{poly}(X)_n\text{poly}(Y)_m \qquad (I)$$

where each X independently is aspartic acid, glutamic acid, phosphoserine, phosphohomoserine, phosphotyrosine, or phosphothreonine, each Y independently is alanine, leucine, isoleucine, valine, glycine or other nonpolar, amino acid residues n is 2 to 60, preferably 15–50, more preferably 30–50, m is 2 to 60, preferably 3–15, more preferably 4–10, n+m is ≧5, preferably n+m is 15–80, more preferably 15–40, and wherein poly $(X)_n$ may contain up to 10% of the Y residues and poly $(Y)_m$ may contain up to 10% of the X residues and salts thereof.

$$\text{poly}(X')_a\text{poly}(Y')_b \qquad (II)$$

where each X' independently is aspartate, glutamate, glutamine, asparagine, or anionic derivatives of these amino acids, or phosphoserine, each Y' independently is a phosphorylated amino acid such as phosphoserine, phosphohomoserine, phosphotyrosine, phosphothreonine, phosphoglutamine, phosphoasparagine or mixtures of these residues, a is 2 to 150, b is 1 to 3, and a+b is ≧5, and salts of these peptides, particularly those with physiologically acceptable anions and cations.

As can be seen from the general formula (I), the anionic amino acids in the polypeptides of formula (I) are clustered on one end of the amino acid chain, whereas the nonpolar amino acids are clustered on the other end. Thus, these polypeptides are not random copolymers. In the formula (I), the X amino acids may either be at the C-terminus or the N-terminus. In other words, the aspartic acid, glutamic acid, etc., residues may be segregated at the N-terminus or the C-terminus.

The X amino acids may be entirely comprised of any one of the X group, or may be any combination of members of the group. Similarly, the Y amino acids may be entirely any one of the Y group, or may be any combination of members of the group. For example, poly (X) could be made up entirely of phosphorylated amino acids.

Peptides wherein up to 10% of the X (anionic) residues are replaced by Y (non-polar) residues and vice versa are also within the scope of this invention. To illustrate this possibility, the following peptide is considered.

$$H_2N\text{-}(Ala)_{10}\text{-}(Asp)_{10}\text{-}OH$$

The Y residues are ten alanines. One of these residues (10%) could be replaced by an anionic residue (e.g., aspartic acid or glutamic acid). Similarly, the X residues are ten aspartic acid residues. One of these could be replaced by a non-polar amino acid (e.g., alanine, glycine, valine, etc.). Naturally, only integral numbers of replacement amino acids are possible.

Specific preferred examples of formulas of polypeptides of formula (I) are the following:

$H_2N\text{-}(Asp)_n\text{-}(Ala)_m\text{-}OH$
$H_2N\text{-}(Ala)_m\text{-}(Asp)_n\text{-}OH$
$H_2N\text{-}(pSer)_n\text{-}(Ala)_m\text{-}OH$
$H_2N\text{-}(Ala)_m\text{-}(pSer)_n\text{-}OH$
$H_2N\text{-}(Glu)_n\text{-}(Ala)_m\text{-}OH$
$H_2N\text{-}(Ala)_m\text{-}(Glu)_n\text{-}OH$
$H_2N\text{-}(Ala)_m\text{-}(Asp)_n\text{-}(pSer)_x\text{-}OH$
$H_2N\text{-}(Ala)_m\text{-}(Glu)_n\text{-}(pSer)_x\text{-}OH$ wherein:

n=10–60, preferably 15–50.

m=2–10, preferably 3–8.

x=2–5, preferably 2–3.

[pSer=phosphoserine; that is, serine which has been phosphorylated on the side chain hydroxyl].

In each of the above formulas, some or all of the alanine residues may be replaced by other nonpolar amino acids, such as leucine, isoleucine, valine and glycine. Similarly, some or all of the aspartic acid residues may be replaced by other anionic amino acids such as glutamic acid, and vice versa. Further, some of the glutamic acid residues or aspartic acid residues may be replaced by phosphoserine, phosphohomoserine, phosphotyrosine, phosphothreonine or other phosphorylated amino acids. Generally, amino acids containing a free hydroxyl group can be phosphorylated on the hydroxyl group. The phosphoserines could also be phosphohomoserine, phosphotyrosine, or phosphothreonine.

Some specific preferred embodiments of the polypeptide of formula (I) are the following compounds:

$H_2N\text{-}(Ala)_8\text{-}(Asp)_{18}\text{-}(pSer)_2\text{-}OH$
$H_2N\text{-}(Ala)_8\text{-}(Asp)_{15}\text{-}OH$
$H_2N\text{-}(Ala)_8\text{-}(Asp)_{40}\text{-}OH$
$H_2N\text{-}(Asp)_{20}\text{-}(Ala)_8\text{-}OH$

As can be seen from the above description of the compounds of formula (I), a large number of polypeptides fall within the scope of the present invention. However, each of them has in common the structural feature of clustered hydrophobic or nonpolar amino acids on one end of the polypeptide and clustered anionic amino acids on the other end of the polypeptide. They are also generally small polypeptides having from 10-80 amino acid residues, preferably 10-60 amino acid residues, most preferably 20-50 amino acid residues.

In the above formula (II), both X' and Y' may be phosphoserine, so that polyphosphoserine molecules are included. However, preferably, if X' is phosphoserine, Y' is other than phosphoserine. In another preferred embodiment, X' is aspartate or glutamate, particularly preferably aspartate. Y' is particularly preferably phosphoserine.

By anionic derivatives of the amino acids of X', it is meant that the amino acid (i.e. aspartate, glutamate, asparagine, or glutamine) is phosphorylated, sulfated, phosphonated or sulfonated. Preferably, the side chain of the amino acid is treated with an appropriate reagent to result in one or more (e.g. 1-3), preferably one, phosphate, sulfate, phosphonate, or sulfonate moiety. If the α-amino group of the peptide is available for reaction, it may also be phosphorylated, sulfated, phosphonated or sulfonated. These derivatives can be prepared by the transamidation reaction of Fong and Kowalski, U.S. Pat. No. 4,678,840 (1987), which is incorporated herein by reference.

The Y' residue may be a phosphorylated amino acid selected from the following group:

The number of Y' amino acids, b, is preferably 2-3, particularly preferably 2.

The number of X' residues, a, is preferably 10-50, particularly preferably 15-45, most preferably 30-40.

The sum of a+b is preferably greater than or equal to 5, particularly preferably greater than or equal to 10. The maximum of a+b is 153.

The chemical connections between the X' residues, the Y' residues and the X'-Y' residues is generally an amide bond, connected by way of the alpha amino and carboxyl groups of two amino acids. However, it is also within the scope of the present invention to have bonds between the alpha amino group of one amino acid and the beta carboxyl group of an aspartate residue, or between the alpha amino group of one amino acid and the gamma carboxyl group of a glutamic acid residue. These types of bonds may also occur in the compounds of formula (I).

The X, Y, X', and Y' amino acid residues will generally be L-amino acids. However, it is also possible for the X, Y, X', and/or Y' residues to be D-amino acids, or the peptide/polypeptide molecule may be made up of a combination of D and L residues, such as a racemic mixture.

The X' residues may be connected to the Y' residues by way of a carboxyl group of an X' residue and an amino group of a Y' residue (C-terminus X' residue), or between a carboxyl group of a Y' residue and an amino group of an X' residue (N-terminus X' residue).

Particularly preferred subgenera of compounds and species, of formula (II) are shown herein below:

H-(pSer)$_1$-(Asp)$_{15-45}$-OH, preferably
H-(pSer)$_1$-(Asp)$_{40}$-OH
H-(pSer)$_2$-(Asp)$_{15-45}$-OH, preferably
H-(pSer)$_2$-(Asp)$_{40}$-OH
H-(pSer)$_1$-(pTyr)$_{15-45}$-OH, preferably
H-(pSer)$_1$-(pTyr)$_{40}$-OH
H-(Asp)$_{15-40}$-(pSer)$_1$-OH, preferably
H-(Asp)$_{40}$-(pSer)$_1$-OH
H-(Asp,Glu)$_{15-45}$-(pSer)$_1$-OH (aspartate, glutamate copolymer)
H-(pSer)$_1$-(Asp,Glu)$_{15-45}$-OH etc. (e.g., salts, mixed salts). The abbreviations used herein are defined as follows:

pSer: phosphoserine
Asp: aspartate, aspartic acid
Glu: glutamate, glutamic acid
Tyr: tyrosine
pTyr: phosphotyrosine
pHomoser: phosphohomoserine
pThr: phosphothreonine
pGln: phosphoglutamine
pAsn: phosphoasparagine The acidic side chains of the amino acid residues making up the present molecules may be in protonated form or may be in a salt form, or a mixture thereof. For example, the aspartate residues may be protonated so that they are aspartic acid residues, and the glutamate residues may be protonated so that they are glutamic acid residues. Similarly, the anionic derivatives of the amino acids may be in anionic form (e.g. sulfate, phosphonate, sulfonate), or may be protonated.

Salts of any of the acidic residues set forth above in either formula (I) or (II), especially the sodium and potassium salts, are also within the scope of this invention. When phosphorylated amino acids are incorporated in the compounds, they may be present as salts, e.g., $Ca^{+2}$, $Mg^{+2}$, di-$Na^+$, di-$K^+$, and the like. Salts may also be with transition metals such as zinc, aluminum, nickel and copper, preferably zinc and aluminum. Further, salts of the amino group, such as the p-toluenesulfonate, acetate, etc. are also contemplated.

With respect to the salt forms of the above-identified molecules, it is to be noted that the zinc and aluminum salts may be preferred, since it is known that zinc and aluminum salts of other molecules can inhibit mineral deposition. For example, U.S. Pat. No. 4,522,806 (1985) by H. R. Muhlemann and I. P. Sayer mentions oral compositions and zinc salts. In addition, U.S. Pat. Nos. 4,100,269 (1978) and 4,152,418 (1979) deal with zinc and tartar-control toothpaste.

The cations that seem to be the best mineralization inhibitors are $Zn^{2+}$ and $Al^{3+}$; however, others such as $Mg^{2+}$, $Cu^{2+}$, and $Ni^{2+}$ have been studied and also appear to be useful. Accordingly, it is contemplated that the present invention is not limited to specific salts mentioned herein, and that other cationic metal salts of the present peptides, particularly cationic transition metal salts, could be formed and used for the purposes described herein.

It is also possible, and within the scope of the present invention, to have physical combinations of conventional dispersing agents and one or more of the present compounds. Such compositions may exert a synergistic effect in terms of dispersion stabilization, as is the case for crystallization inhibitors as described in Sikes and Wheeler, *CHEMTECH*, October 1988, 620–626.

The polyamino acids of formulae (I) and (II) may be prepared as described in U.S. Pat. No. 4,868,287 and U.S. patent application Ser. No. 07/339,672 filed Apr. 18, 1989, which are incorporated herein by reference.

Thus, compounds of formulae (I) and (II) may be synthesized by any number of techniques now available for synthesis of simple and complex low molecular weight polypeptides. Generally speaking, these techniques involve stepwise synthesis by successive additions of amino acids to produce progressively larger molecules. The amino acids are linked together by condensation between the carboxyl group of one amino acid and the amino group of another amino acid to form a peptide bond. To control these reactions, it is necessary to block the amino group of one amino acid and the carboxyl group of the other. The blocking groups should be selected for easy removal without adversely affecting the polypeptides, either by racemization or by hydrolysis of formed peptide bonds. Certain amino acids have additional functional groups such as the carboxyl groups of aspartic acid and glutamic acid and the hydroxyl groups of serine, homoserine and tyrosine. It is usually necessary to block these additional groups with an easily removed blocking agent, so that they do not interfere with the desired condensation for the formation of peptide bonds.

A wide variety of procedures exist for the synthesis of polypeptides, and a wide variety of blocking agents have also been devised. Most of these procedures are applicable to the peptides of the present invention. The preferred method for synthesis of the peptides of formulae (I) and (II) is a solid-phase technique. In this procedure, an amino acid is bound to a resin particle, and the peptide is generated in a stepwise manner by successive additions of protected amino acids to the growing chain. The general procedure is well known, and has been described in many articles, for example: Merrifield, R. B., *J. Am. Chem. Soc.* 96, 2986–2993, 1964.

In one aspect of the present invention, the compounds of formulae (I) and (II) may be used to stabilize a mineral dispersion. Thus, the present invention relates to a method of stabilizing an aqueous mineral dispersion comprising adding a compound of formula (I) or (II) to said dispersion. The present invention also relates to stabilized aqueous mineral dispersions containing a mineral and a compound of formula (I) or (II).

In the present method and dispersions, the mineral may be any mineral particle having cationic surfaces. Examples include iron oxide, kaolin, calcium carbonate, calcium phosphate and/or any of the inorganic pigments listed in Kirk Othmer, *Encyclopedia of Chemical Technology*, vol. 17, Wiley, N.Y., pp. 790–793 (1982), which is incorporated herein by reference. Of course, the dispersion may contain other minerals, in addition to those mentioned, and other nonmineral components, as well. The concentration of the mineral in the dispersion is suitably>0 to 80% by weight, preferably 0.01 to 50%, most preferably 0.1 to 30%, and the concentration of the compound of formula (I) or (II) is suitably 0.01 to 800 μ/ml, preferably 0.1 to 300 μ/ml, most preferably 1.0 to 100 μ/ml. Examples of such stabilized dispersions include, for example, paints, cosmetics, boiler water, cooling water, and paper-processing fluids.

The present invention also relates to detersive systems which contain a compound of formula (I) or (II). In addition to the present polyamino acids, the present detersive system may contain the conventional ingredients of detersive systems. Conventional additives of detersive systems are discussed in Kirk-Othmer, *Encyclopedia of Chemical Technology*, Vol. 22, pp. 332–432 (1983), which is incorporated herein by reference. Thus, the present detersive systems may also contain conventional anionic surfactants, including, e.g., carboxylates, such as soaps, polyalkoxycarboxylates, N-acylsarcosinates, acylated protein hydrolysates, sulfonates, alkylbenzenesulfonates, short-chain alkylarenesulfonates, lignosulfonates, naphthalenesulfonates, α-olefinsulfonates, petroleum sulfonates, sulfonates with ester, amide or ether linkages, sulfates and sulfated products, alcohol sulfates, ethoxylated and sulfated alcohols, ethoxylated and sulfated alkylphenols, sulfated acids, amides, and esters, sulfated natural oils and fats, and phosphate esters.

The present detersive systems may also contain nonionic surfactants, including polyoxyethylene surfactants (ethoxylates), such as alcohols ethoxylates and alkylphenol ethoxylates, carboxylic acid esters, such as glycerol esters, polyoxyethylene esters, anhydrosorbitol esters, ethoxylated anhydrosorbitol esters, ethoxylated natural fats, oil and waxes, and glycol esters of fatty acids, carboxylic amides, diethanolamine condensates, monoalkanolamine condensates, polyoxyethylene fatty acid amides, and polyalkylene oxide block copolymers, such as poly(oxyethylene-co-oxypropylene) nonionic surfactants.

The present detersive systems may also contain conventional cationic surfactants, including amines, such as oxygen-free amines (e.g., aliphatic mono, di-, and polyamines derived from fatty and resin acids) and oxygen containing amines other than amides (e.g., amine oxides and alkyl amine ethoxylates), 2-alkyl-1-(2-hydroxyethyl)-2-imidazolines, amines with amide linkages, and quaternary ammonium salts.

The present detersive systems may also include conventional amphoteric surfactants, including imidazolium derivatives.

The present detersive systems may be formulated by any conventional method and to include other conventional additives in addition to the surfactants described above. Thus, the present detergents may include conventional builders such as, phosphates (e.g., $Na_5P_3O_{10}$, $Na_4P_2O_7$, $Na_3PO_4$, glassy phosphates and potassium phosphates), sodium carbonate, silicates (e.g., sodium silicates), zeolites (e.g., type A), clays (e.g., kaolin, montmorillonites, and bentonites), nitrilotriacetic acid, alkalies, (e.g., NaOH), and neutral soluble salts (e.g., $Na_2SO_4$).

The present detersive systems may also contain other conventional organic additives, including: conventional antiredeposition agents, such as carboxymethylcellulose (NaCMC), methylcellulose, hydroxybutylcellulose, hydroxypropyl- and mixed methyl and hydroxylbutyl cellulose ethers; fluorescent whitening agents; bluing agents; bleaching agents, such as $NaBO_3 \cdot 4H_2O$, chlorinated trisodium orthophosphate and chlorinated isocyanurate; foam regulators, such as amine oxides and alkanolamides; and organic sequestering agents, such as EDTA.

The present detersive systems include liquids and powders. The liquid detersive systems may be prepared by metering and mixing the individual ingredients in the proper amounts. The powder detersive systems may be prepared as either spray-dried powders, dry-blended powders, or agglomerated powders by conventional techniques, such as those described in Kirk-Othmer, *Encyclopedia of Chemical Technology*, Vol. 22, pp. 332–432 (1983).

In the present detersive systems, the compounds of formulae (I) and (II) are suitably present in an amount of 0.1 to 50.0 wt. %, preferably 0.1 to 30 wt. %, most preferably 1 to 10 wt. %.

The present invention also relates to cosmetics, such as shampoos and body soaps, which contain the compounds of formula (I) or (II). In addition to the compounds of formulae (I) and (II), the present shampoos may contain other conventional additives and ingredients. Conventional additives and ingredients for shampoos are discussed in Kirk-Othmer, *Encyclopedia of Chemical Technology*, Vol. 7, pp. 163–168 (1979), which is incorporated herein by reference. Thus, the present shampoos may contain: detergents, such as fatty alcohol sulfates, ether sulfates, sarcosinates, and alkanolamides; soft soaps; sulfonated oils, such as sulfonated castor oil and sulfonated olive oil; preservatives; coloring agents; perfumes; anionic surfactants; amphoteric surfactants, such as imidazoline, betaine, and sulfobetaine surfactants; antidandruff agents, such as coal tar, quaternary ammonium compounds, resorcinol, salicylic acid, selenium sulfide, sulfur, undecylenic acid and derivatives, and zinc pyrithione; foam builders; conditioning agents; opacifying agents; sequestering agents, such as citric acid, tartaric acid, and salts of EDTA; and viscosity builders.

In the present shampoos, the compounds of formulae (I) and (II) are suitably present in an amount of 0.1 to 50 wt. %, preferably 0.1 to 30 wt. %, most preferably 1 to 10 wt. %.

The present invention also relates to body and facial soaps which contain a compound of formula (I) or (II). The present soaps may be prepared according to conventional methods as described in Kirk-Othmer, *Encyclopedia of Chemical Technology*, Vol. 21, pp. 162–181 (1983), which is incorporated herein by reference. Thus, the present soaps may contain, in addition to the compounds of formulae (I) and (II), any conventional metal salt of a long-chain monocarboxylic acid and conventional additives, including: antibacterial agents, such as 3,4,4'-trichlorocarbanilide and 2-hydroxy-2', 4,4'-trichlorodiphenyl ether; superfatting agents, such as unsaponified oils, fatty acids, or lanolin, mineral oil, fatty esters, and fatty alcohols; transparency agents, such as alcohol, sugar, and glycerin; abrasives, such as pumice; and builders, such as sodium silicate, sodium carbonate, and trisodium phosphate.

The present soaps may be in the form of a bar, a powder, or a liquid. The compounds of formulae (I) and (II) are suitably present in an amount of 0.1 to 50 wt. %, preferably 0.1 to 30 wt. %, most preferably 1 to 10 wt. %.

Other features of the invention will become apparent in the course of the following descriptions of exemplary embodiments which are given for illustration of the invention and are not intended to be limiting thereof.

EXAMPLES

Synthesis of the Polypeptides:

An automated, solid-phase synthesizer (Applied Biosystems, Model 430A) was used to prepare peptides of precisely known sequence and molecular size. The t-Boc strategy of terminal amine protection was used with aspartic acid supplied as t-Boc-L-aspartic acid with beta carboxyl protection by O-benzyl linkage. Similarly, serine was supplied as t-Boc-L-serine-O-benzyl.

In all cases, coupling efficiency of each residue was checked by automated sampling of peptide resin for measurement of unreacted free amine by the ninhydrin method (Sarin, V. K., et al., *Anal. Bioch.* Vol. 117, pp. 147–157 (1981)). Coupling efficiencies routinely were greater than 99% per cycle of synthesis.

The carboxy terminal amino acid was preloaded via an organic linker (PAM, 4-oxymethyl phenylacetamidomethyl) covalently attached to an insoluble polystyrene resin cross-linked with divinyl benzene.

In this preferred embodiment, the C-terminus of the polypeptides was aspartate and the C-terminal region polyanionic, with hydrophobic residues added to the polypeptides on the N-terminus. The reason for this orientation is that the aspartate-PAM linkage is easier to cleave at the end of the synthesis as compared to hydrophobic amino acid-PAM linkages, resulting in greater yields. It is not likely that the positioning of the polyanionic or hydrophobic regions at the C- vs. the N-terminus matters with regard to activity.

Following synthesis, peptide-resin was repeatedly washed with methanol then dried and weighed. Then peptides were cleaved from the resin using a modification of the trifluoromethanesulfonic acid (TFMSA) procedure, with precautions taken to prevent aspartimide formation (Bergot, J. B., et al., *Applied Biosystems Bulletin* (1986)). For 100 mg samples, peptide-resins in a scintillation vial were treated for 10 minutes with 150 μl of anisole to swell the resin, making it more accessible for reaction. Then 1.0 ml of neat trifluoroacetic acid (TFA) was added with magnetic stirring and allowed to react for 10 minutes. Next, 100 μl of concentrated TFMSA (Aldrich Chemical Co.) were added with cooling using an ice bath, followed by cleavage of the peptide from the resin at room temperature for 30 minutes. For cleavage of other amounts of peptide-resin, the amounts of reagents used were changed proportionally.

Following cleavage, 20 ml of methyl butyl ether (MBE) (Aldrich) were added to the vial to ensure precipitation of the peptide, which already was relatively insoluble in the acidic reaction medium due to the acidic nature of the peptides. After stirring for 1–2 minutes, the entire slurry was passed through a 4.25 cm glass fiber filter (Fisher G4) using a filter funnel and vacuum pump at 15 psi. This removed the TFA, TFMSA, anisole, and any soluble reaction products, leaving the cleaved peptide and resin on the filter.

Extraction of Metal Salts of the Peptides:

After washing on the filter with 100 ml of MBE, the acid form of the peptides was converted into a soluble sodium salt by extraction into a clean, dry flask with 10 ml of $Na_2CO_3$(0.02M, pH 10.2), using 5 successive rinses of 2 ml, with at least 1 minute extraction on the filter prior to applying the vacuum each time. Conversion of the peptides to other metal adducts such as Zn or Al forms may be accomplished by adding an excess of soluble salts of the metals; for example, $ZnCl_2$ or $AlCl_3$, to the $Na_2CO_3$ solution used for the extraction.

Purification of the Peptides:

Upon extraction, the filtrate containing the solubilized peptides had pH values>5. The filtrate was then dialyzed twice with stirring against 2 liters of distilled water for 2 hours using dialysis tubing (Spectrapor, nominal MW cutoff of 1000 daltons). The dialysate was frozen and lyophilized, yielding white flakes or powders. The average yield of the peptides was 40%.

Following isolation, purity of the peptides was checked by high performance liquid chromatography (Varian 5500 LC) using gel permeation columns designed for separations of peptides (Toya Soda 2000 SW and 3000 PWXL). Single, sharp peaks at the appropriate MW's were obtained.

Because the peptides were isolated partially as sodium salts, the sodium content was determined by atomic absorption (Perkin Elmer model 360). Sodium levels typically were less than 5% by weight. Amounts of peptides reported are corrected for sodium content. Concentrations of peptides in aqueous stock solution were based on lyophilized dry weight but were also checked by comparison of UV spectra.

Thermal Peptide Synthesis:

Peptides of approximately known sequence and size were made by thermal polymerization of amino acids (Fox, S. W. and K. Harada, "Thermal polycondensation of alpha-amino acids" in *A Laboratory Manual of Analytical Methods of Protein Chemistry*, Vol. 4, P. Alexander and H. P. Lundgren (eds.), 1966, pp. 127–151). For example, L-aspartic acid (500 g) was placed in a two-liter, round-bottom reaction vessel, originally designed as the evaporator vessel in a rotary evaporator apparatus. The reaction vessel was partially submerged in cooking oil in a deep-fryer set at 190° C. (±2° C.). The reaction vessel was coupled by ground glass fitting to a condenser vessel, which in turn was fitted to a rotator shaft 'driven by a rheostated electric motor. The fittings were sealed with tape and fastened with hose clamps. A stream of nitrogen was continuously purged into the condenser vessel to eliminate O2 and the possibility of charring. The reaction was allowed to continue for up to 24 hours at which time no further visible evolution of water vapor was observed. The water is produced as a result of the dehydration reaction of peptide bond formation and serves as a good indicator of the progress of the reaction.

Polyaspartate molecules of approximately 5000 daltons (determined by gel permeation) were produced. They were purified by dissolving at pH 6 in water followed by dialysis to remove unreacted aspartic acid, although the bulk product is also usable without further purification.

Polyanionic/hydrophobic peptides of approximately-known sequence and size may also be made by conventional thermal polymerization of the polyanionic region and the hydrophobic regions separately using R-group protected amino acids (Melius, P. and J. Y. P. Sheng, *Bioorg. Chem.*, Vol. 4, pp. 385 (1975)). Next, the polyanionic and hydrophobic regions can be linked thermally, followed by deprotection of the R-groups using cleavage reagents. There is some evidence to suggest that a polyanionic/hydrophobic peptide may assemble naturally under thermal polymerization conditions, without the need for separate synthesis followed by attachment of the two regions (Phillips, R. D. and P. Melius, *Int. J. Peptide Protein Res.*, Vol. 6, pp. 309–319 (1974)).

Phosphorylation of Peptides:

Serine residues attached at either the N-terminus or the C-terminus were phosphorylated via the method of Neuhaus and Korkes (1958). Phosphorus oxychloride, $POCl_3$ was added as 117 ml (1.25 moles) to 45 ml (2.5 moles) of water. This solution was stirred for one hour, allowing formation of monochlorophosphate ($ClH_2PO_3$). Next, amounts up to 0.25 moles of peptides were added with stirring and occasional heating at 60° C. for two hours. The reaction was ended by dropwise addition of 18 ml (1 mole) of $H_2O$ to degrade any unreacted monochlorophosphate to orthophosphate. Any polyphosphates that may have formed during the reaction were destroyed by addition of 75 ml of 1N HCl and heating in a boiling water bath for at least 20 minutes. Upon cooling, peptides were crystallized in 95 percent ethanol and methyl butyl ether at 3° C. overnight. Crystals were washed repeatedly with ethanol. The extent of phosphorylation of peptides was monitored spectrophotometrically by formation of the phosphomolybdate complex (Eisenreich et al., *Environmental Letters*, Vol. 9, pp. 43–53(1975)).

Industrial Polymers:

Industrial polymers were acquired from water-treatment chemical companies. A 4–5 kD polyacrylate (Buckman Chemical Co.) is a widely used commercial dispersant. A 5–8 kD terpolymer of acrylic acid, acrylamide, and acrylamide-alkyl sulfonate (Nalco Chemical Co.) is representative of a new generation of commercial dispersants.

Mineral Particles:

Kaolin (an aluminum silicate) was chosen for study to represent dispersions of clay or soil particles. Iron oxide is a common mineral that requires dispersion in boiler and cooling water. Calcium hydroxyapatite and carbonate are also common problem minerals encountered in water treatment. In addition, calcium hydroxyapatite is a major constituent of dental tartar and dispersion of both calcium carbonate and kaolin is used in providing fillers and pigments in paper. Thus, the mineral particles studied were chosen to represent a wide variety of dispersion applications.

Example 1. Kaolin Dispersion 500 mg kaolin (Sigma; particle size 0.1–4.0 µm) was weighed and placed in a 600 ml beaker. Distilled water was added to the 400 ml mark. 1 ml of 0.5M $MgCl_2 \cdot 6 H_2O$; 1.8 ml of 1.0M $CaCl_2 \cdot 2H_2O$; and 4.5 ml of 0.4M $NaHCO_3$ were added to the solution in the order presented. This added ionic strength, simulating hard water. $Mg^{+2}$ helped to prevent $CaCO_3$ precipitation in solution or at the surface of the kaolin. Microliter amounts of 1N NaOH were added to bring the pH to 8.50. Approximately 90 ml of distilled $H_2O$ were added to bring the final volume to 500 mls, resulting in a concentration of 1.0 mM $MgCl_2$, 3.6 mM $CaCl_2$, and 3.6 mM $NaHCO_3$.

Figure 1:
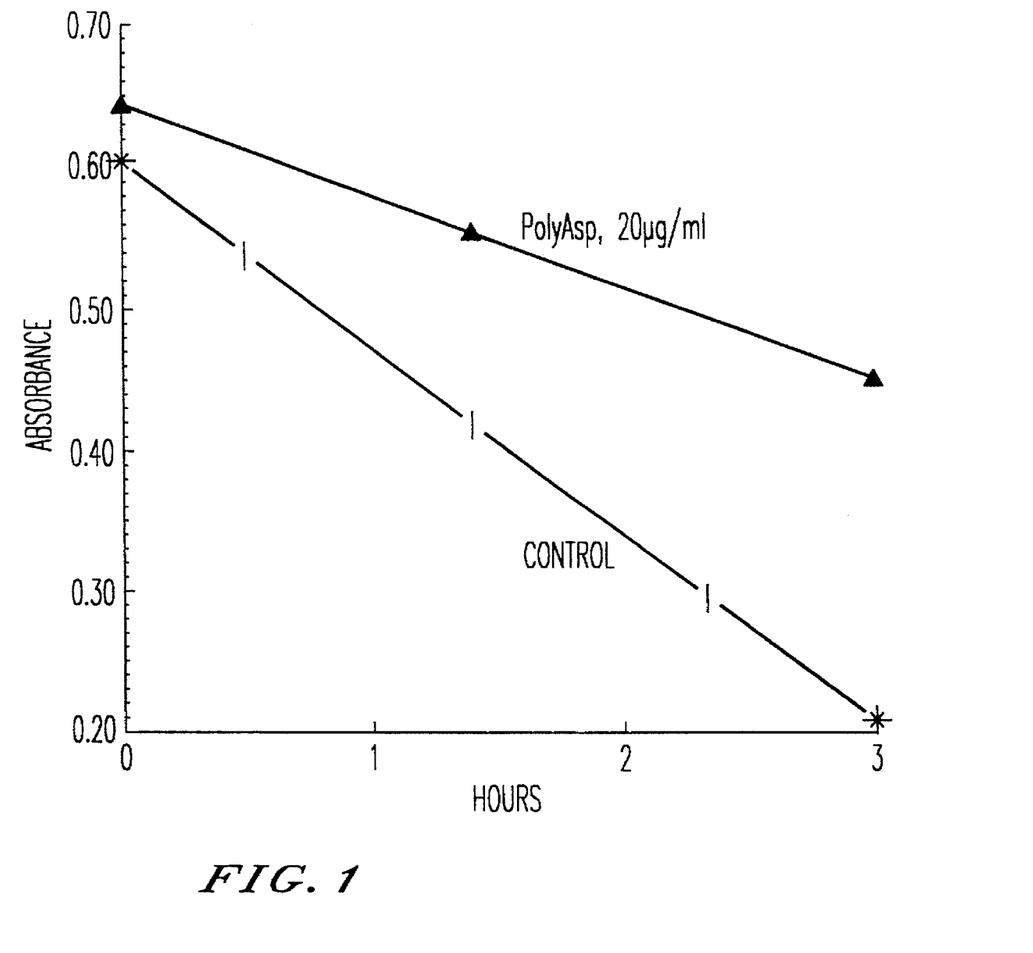
FIG. 1 illustrates the measurement of dispersion of kaolin (control, +, polyasp, -▲-)

50 ml aliquots were placed in 2 oz. (60 ml) vials. The vials (9) were placed on a multiple magnetic stirring plate in a recirculating water bath at 20° C. Peptide or polymer was added at a concentration of 10 µ/ml, and the suspensions were stirred for one hour. While the vials were still being stirred, an initial sample (3 mls) was taken at 1.5 cm below the surface and placed in a 4 ml disposable cuvette. The samples were gently agitated and turbidity was measured by absorbance using a spectrophotometer (Perkin Elmer lambda 4) at 500 nm. The stirring was stopped immediately after the initial sampling. After 30 minutes, a final sample was taken at 1.5 cm below the surface. The amount of absorbance was measured and recorded. The results are shown in FIG. 1 and Table 1.

TABLE 1

Kaolin Dispersion

| Sample | Absorbance ± S.D. | n | Amount of Dispersant (μg/ml) |
|---|---|---|---|
| Control | 0.2943 ± 0.0232 | 18 | — |
| HO—Asp$_{30}$Ala$_8$—H | 0.4208 ± 0.0279 | 6 | 10 |
| H—PSer$_2$Asp$_{15}$Ala$_8$—OH | 0.3962 ± 0.0354 | 6 | 10 |
| HO—Asp$_{20}$Ala$_8$—H | 0.3883 ± 0.0031 | 3 | 10 |
| HO—Asp$_{20}$Ala$_{20}$—H | 0.3523 ± 0.0342 | 6 | 10 |
| H—PSer$_2$Asp$_{20}$—OH | 0.3397 ± 0.0273 | 6 | 10 |
| Polyaspartate | 0.3192 ± 0.0215 | 9 | 10 |

Absorbance @ 500 nm after settling for 30 minutes.

Example 2. Iron Oxide Dispersion

Particulate iron oxide dispersion was measured with calcium present because divalent ions such as calcium interfere with the activity of conventional polymers. Samples that did not contain calcium served as controls.

Figure 2:
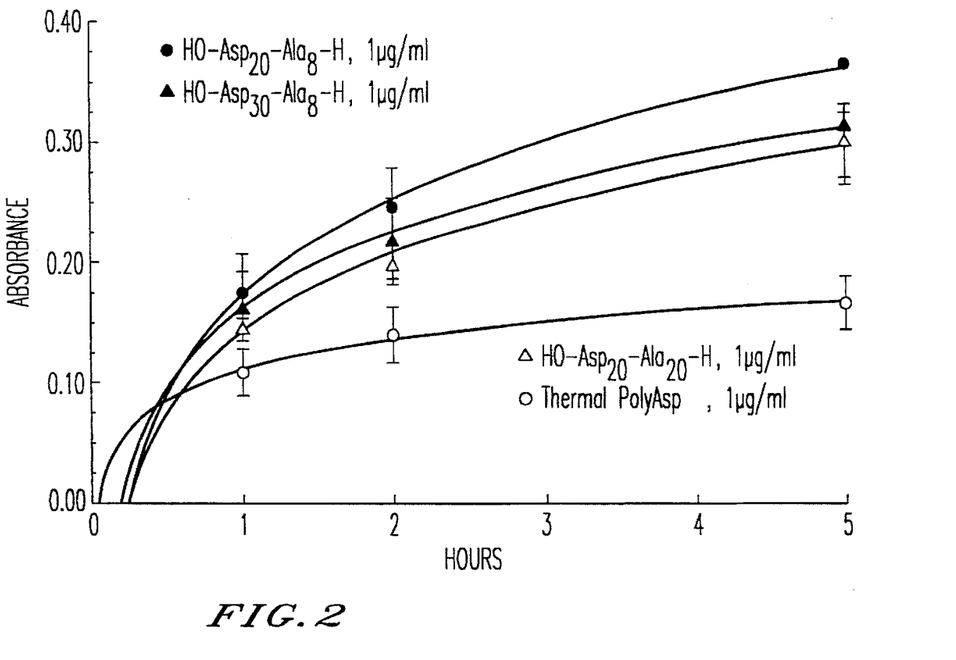
Figure 3:
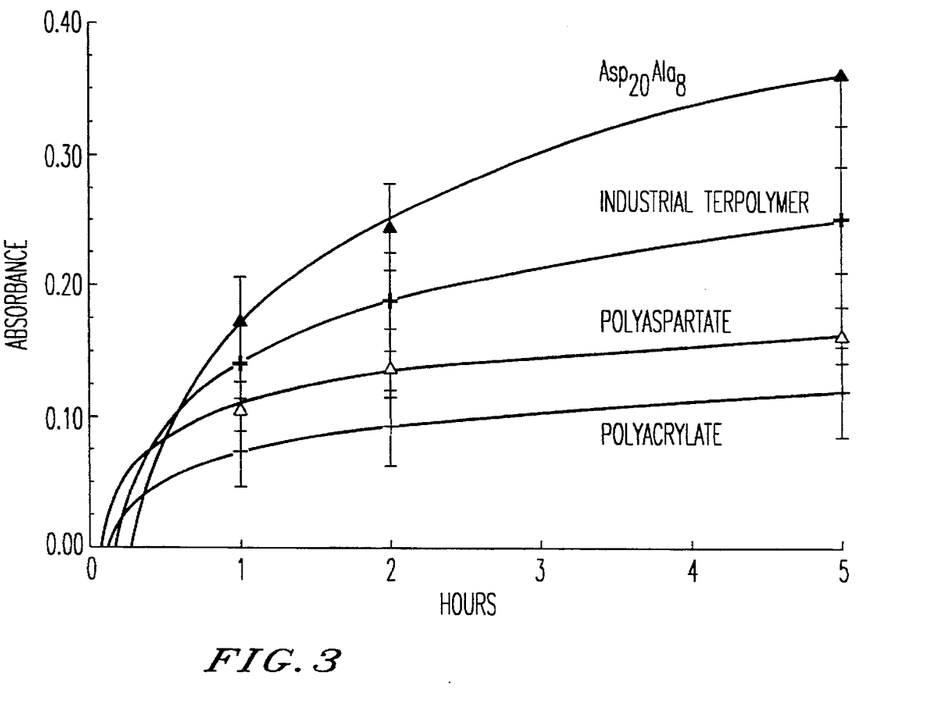
Figure 4:
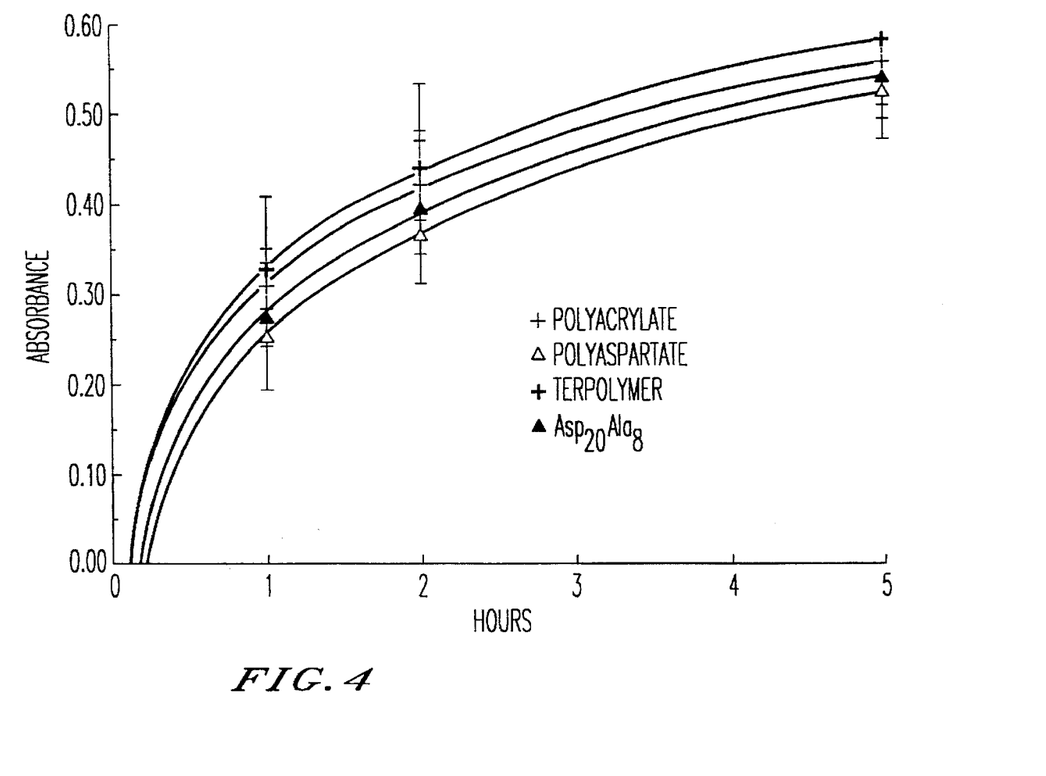
FIG. 4 illustrates the efficacy of various dispersing agents for stabilizing an aqueous dispersion of iron oxide in which calcium is not present, polyacrylate, +; polyaspartate, △; terpolymer, +; and $Asp_{20}Ala_8$, ▲.

Six 1000 ml beakers were filled with 950 ml of distilled water. One mg of polymer or peptide and 9 ml of 0.4M NaHCO$_3$ (Fisher) were added to all six beakers. Next, 3.6 ml of 1.0M CaCl$_2$ (Fisher) were added to only three beakers. All beakers were titrated to pH 8.5 with μl amounts of 1N NaOH or 1N HCl. The solutions were brought to final volume in 1000 ml volumetric flasks. Finally, a slurry was made in the beakers with 100 mg Fe$_2$O$_3$ (Fisher) with small amounts of distilled water and the appropriate volumetric solutions. All beakers were placed on a multiple magnetic stir plate submerged in a recirculating bath (VWR model 1155) maintained at 20° C. Aliquots of 3 ml were taken at 0, 1, 2, and 5 hours at a depth of 1 cm and placed in a 4 ml disposable cuvette. Each sample was resuspended and read at 500 nm using a spectrophotometer (Perkin Elmer lambda 4). Elevated absorbance versus time relative to control values indicated better dispersion stabilizing activity. The results are shown in Table 2 and FIGS. 2–4.

TABLE 2

Iron Oxide Dispersion

| Sample | Absorbance ± S.D. | n | Dose (μg/ml) |
|---|---|---|---|
| HO—Asp$_{20}$Ala$_8$—H | 0.3653 ± 0.0403 | 6 | 1.0 |
| HO—Asp$_{20}$Ala$_{20}$—H | 0.3162 ± 0.0442 | 6 | 1.0 |
| HO—Asp$_{30}$Ala$_8$—H | 0.3147 ± 0.0482 | 3 | 1.0 |
| H—PSer$_2$Asp$_{15}$Ala$_8$—OH | 0.2888 ± 0.0303 | 6 | 1.0 |
| Terpolymer | 0.2543 ± 0.0398 | 6 | 1.0 |
| PolyAsp(thermal) | 0.1667 ± 0.0226 | 6 | 1.0 |
| Polyacrylate | 0.1220 ± 0.0345 | 6 | 1.0 | absorbance @ 500 nm at 5 hours.

Example 3. Calcium Phosphate

First, 1 g of hydroxyapatite (Aldrich calcium phosphate tribasic) was suspended in a 1 liter solution of 1 mM NaHCO$_3$ (Fisher) in distilled water. The solution was adjusted to pH 8.0. After vigorous shaking, a 3.0 ml aliquot was pipetted from the center of the stock solution, and placed in a 4.0 ml glass cuvette, resuspended, and placed in a water-jacketed cell holder at 20° C. The crystals were allowed to settle in the cuvette for 20 minutes. The settling was continuously monitored using a spectrophotometer (Perkin Elmer lambda 4) at 500 nm.

Figure 5:
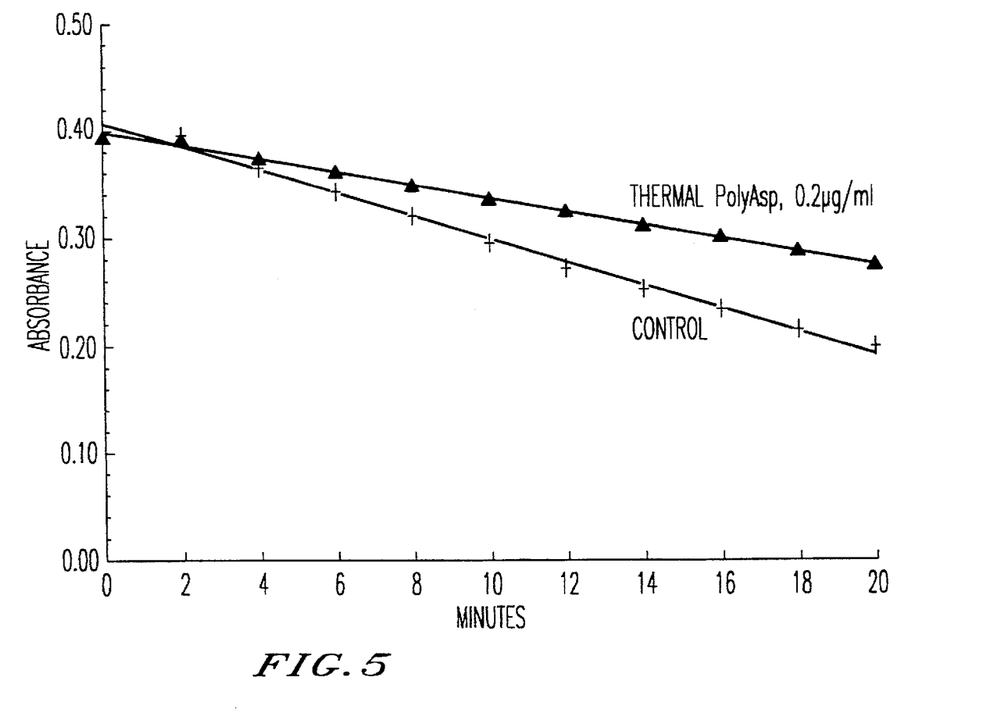
FIG. 5 illustrates the measurement of stabilizing an aqueous dispersion of calcium hydroxyapatite, control, +; and thermal polyasp, ▲.

After the initial and final absorbances were recorded, 0.2 μ/ml of the polymer or peptide was added to the sample. The sample was resuspended and allowed to settle for 20 minutes in the cuvette. The difference between the control slope and the experimental slope was used to determine dispersion activity. A slower settling rate is characteristic of better dispersion activity. The results are shown in FIG. 5 and in Table 3.

TABLE 3

Calcium Hydroxyapatite Dispersion

| Sample | Slope$^a$ | S.D. | n | Amount of Dispersant (μg/ml) |
|---|---|---|---|---|
| Control | 0.0098 | ± 0.0006 | 34 | — |
| PolyAsp(thermal) | 0.0057 | ± 0.0002 | 6 | 0.2 |
| Polyacrylate | 0.0056 | ± 0.0012 | 5 | 0.2 |
| Terpolymer | 0.0052 | ± 0.0002 | 5 | 0.2 |
| HO—Asp$_{20}$Ala$_8$—H | 0.0046 | ± 0.0006 | 4 | 0.2 |

$^a$absorbance units/minute.

Example 4. Calcium Carbonate

Fifty mg of calcium carbonate were weighed and placed in each of twelve 2 oz (60 ml) vials. Fifty ml of H$_2$O were added to each vial. Each vial was placed on a multiple magnetic stir plate submerged in a recirculating water bath maintained at 20° C. One hundred μl of 0.5M MgCl$_2$ and 180 μl of 1.0M CaCl$_2$ were added to each slurry to add hardness. Dissolved CaCO$_3$ brought the pH above 8.0. Peptide or polymer was added to each of three vials at concentrations of 0, 1, 2, and 5 μg/m. The set of vials that had no polymer or peptide added served as a control. Aliquots of 3 mls were taken at 0, 5, and 20 hours at a depth of 1.5 cm and placed in a 4 ml disposable cuvette. Each sample was resuspended, and the absorbance was read at 500 nm in a spectrophotometer. Increased dispersion activity was measured by an increase in absorbance.

TABLE 4

Calcium Carbonate Dispersion After 20 Hours in the Presence of Peptide and Polymer Dispersants

| Dispersant | Dose (μg/ml) | Mean Absorbance ± S.D. | n |
|---|---|---|---|
| Control | — | 0.376 ± 0.043 | 32 |
| Polyacrylate | 1 | 0.438 ± 0.043 | 3 |
|  | 2 | 0.482 ± 0.043 | 3 |
|  | 5 | 0.490 ± 0.030 | 3 |
| CX-957 | 1 | 0.422 ± 0.056 | 6 |
| (sulfonated terpolymer) | 2 | 0.486 ± 0.026 | 6 |
|  | 5 | 0.510 ± 0.018 | 5 |
| Polyaspartate | 1 | 0.433 ± 0.027 | 6 |
| (thermal) | 2 | 0.472 ± 0.016 | 5 |
|  | 5 | 0.417 ± 0.024 | 6 |
| HO—Asp$_{30}$—Ala$_8$—H | 1 | 0.467 ± 0.004 | 3 |
|  | 2 | 0.509 ± 0.008 | 3 |
|  | 5 | 0.532 ± 0.026 | 3 |
| HO—Asp$_{20}$—Ala$_8$—H | 1 | 0.444 ± 0.043 | 9 |
|  | 2 | 0.492 ± 0.058 | 9 |
|  | 5 | 0.502 ± 0.022 | 8 |
| HO—Ala$_8$—Asp$_{15}$—PSer$_2$—H | 1 | 0.493 ± 0.027 | 6 |
|  | 2 | 0.532 ± 0.031 | 6 |
|  | 5 | 0.497 ± 0.064 | 6 |

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by Letters Patent of the United States is:

1. A method of stabilizing an aqueous mineral suspension, comprising adding at least one compound having formula (I) or (II) to said suspension:

$$\text{poly}(X)_n\text{poly}(Y)_m \quad (I)$$

where each X independently is aspartic acid, glutamic acid, phosphoserine, phosphohomoserine, phosphotyrosine, or phosphothreonine, each Y independently is alanine, leucine, isoleucine, valine, glycine or other nonpolar, amino acid residues, n is 2 to 60, m is 2 to 60, and n+m is $\geq 5$, and wherein poly $(X)_n$ may contain up to 10% of the Y residues and poly $(Y)_m$ may contain up to 10% of the X residues, and salts thereof; and $$\text{poly}(X')_a\text{poly}(Y')_b \quad (II)$$

where each X' independently is aspartate, glutamate, glutamine, asparagine, or anionic derivatives of these amino acids, or phosphoserine, each Y' independently is a phosphorylated amino acid such as phosphoserine, phosphohomoserine, phosphotyrosine, phosphothreonine, phosphoglutamine, phosphoasparagine or mixtures of these residues, a is 2 to 150, b is 1 to 3, and a+b is $\geq 5$, and salts of these peptides; wherein said suspension contains at least one mineral.

2. A stabilized aqueous mineral suspension, comprising at least one compound having formula (I) or (II):

$$\text{poly}(X)_n\text{poly}(Y)_m \quad (I)$$

where each X independently is aspartic acid, glutamic acid, phosphoserine, phosphohomoserine, phosphotyrosine, or phosphothreonine, each Y independently is alanine, leucine, isoleucine, valine, glycine or other nonpolar, amino acid residues, n is 2 to 60, m is 2 to 60, and n+m is $\geq 5$, and wherein poly $(X)_n$ may contain up to 10% of the Y residues and poly $(Y)_m$ may contain up to 10% of the X residues, and salts thereof; and $$\text{poly}(X')_a\text{poly}(Y')_b \quad (II)$$

where each X' independently is aspartate, glutamate, glutamine, asparagine, or anionic derivatives of these amino acids, or phosphoserine, each Y' independently is a phosphorylated amino acid such as phosphoserine, phosphohomoserine, phosphotyrosine, phosphothreonine, phosphoglutamine, phosphoasparagine or mixtures of these residues, a is 2 to 150, b is 1 to 3, and a+b is $\geq 5$, and salts of these peptides; wherein said suspension contains at least one mineral.

3. The suspension of claim 2, wherein said suspension is a paint.

4. A detersive system, comprising (a) at least one compound having formula (I) or (II):

$$\text{poly}(X)_n\text{poly}(Y)_m \quad (I)$$

where each X independently is aspartic acid, glutamic acid, phosphoserine, phosphohomoserine, phosphotyrosine, or phosphothreonine, each Y independently is alanine, leucine, isoleucine, valine, glycine or other nonpolar, amino acid residues, n is 2 to 60, m is 2 to 60, and n+m is $\geq 5$, and wherein poly $(X)_n$ may contain up to 10% of the Y residues and poly $(Y)_m$ may contain up to 10% of the X residues, and salts thereof; and $$\text{poly}(X')_a\text{poly}(Y')_b \quad (II)$$

where each X' independently is aspartate, glutamate, glutamine, asparagine, or anionic derivatives of these amino acids, or phosphoserine, each Y' independently is a phosphorylated amino acid such as phosphoserine, phosphohomoserine, phosphotyrosine, phosphothreonine, phosphoglutamine, phosphoasparagine or mixtures of these residues, a is 2 to 150, b is 1 to 3, and a+b is $\geq 5$, and salts of these peptides, and (b) one member selected from the group consisting of surfactants, builders, and water.

5. A cosmetic composition suitable for application to human hair and aqueous rinsing therefrom, comprising a compound which is effective for the cleansing of hair and at least one compound having formula (I) or (II):

$$\text{poly}(X)_n\text{poly}(Y)_m \quad (I)$$

where each X independently is aspartic acid, glutamic acid, phosphoserine, phosphohomoserine, phosphotyrosine, or phosphothreonine, each Y independently is alanine, leucine, isoleucine, valine, glycine or other nonpolar, amino acid residues, n is 2 to 60, m is 2 to 60, and n+m is $\geq 5$, and wherein poly $(X)_n$ may contain up to 10% of the Y residues and poly $(Y)_m$ may contain up to 10% of the X residues, and salts thereof; and $$\text{poly}(X')_a\text{poly}(Y')_b \quad (II)$$

where each X' independently is aspartate, glutamate, glutamine, asparagine, or anionic derivatives of these amino acids, or phosphoserine, each Y' independently is a phosphorylated amino acid such as phosphoserine, phosphohomoserine, phosphotyrosine, phosphothreonine, phosphoglutamine, phosphoasparagine or mixtures of these residues, a is 2 to 150, b is 1 to 3, and a+b is $\geq 5$, and salts of these peptides.

6. A cosmetic composition suitable for application to human skin, comprising a compound effective for cleansing human skin and at least one compound having formula (I) or (II):

$$\text{poly}(X)_n\text{poly}(Y)_m \qquad (I)$$

where each X independently is aspartic acid, glutamic acid, phosphoserine, phosphohomoserine, phosphotyrosine, or phosphothreonine, each Y independently is alanine, leucine, isoleucine, valine, glycine or other nonpolar, amino acid residues, n is 2 to 60, m is 2 to 60, and n+m is $\geq 5$, and wherein poly $(X)_n$ may contain up to 10% of the Y residues and poly $(Y)_m$ may contain up to 10% of the X residues, and salts thereof; and $$\text{poly}(X')_a\text{poly}(Y')_b \qquad (II)$$

where each X' independently is aspartate, glutamate, glutamine, asparagine, or anionic derivatives of these amino acids, or phosphoserine, each Y' independently is a phosphorylated amino acid such as phosphoserine, phosphohomoserine, phosphotyrosine, phosphothreonine, phosphoglutamine, phosphoasparagine or mixtures of these residues, a is 2 to 150, b is 1 to 3, and a+b is $\geq 5$, and salts of these peptides.

* * * * *